United States Patent [19]

Shaari

[11] Patent Number: 5,599,304
[45] Date of Patent: Feb. 4, 1997

[54] SINONASAL SUCTION APPARATUS

[75] Inventor: Christopher M. Shaari, New York, N.Y.

[73] Assignee: Mount Sinai School of Medicine of the City University of New York, New York, N.Y.

[21] Appl. No.: 240,865

[22] Filed: May 10, 1994

[51] Int. Cl.$^6$ .................................................. A61M 11/00
[52] U.S. Cl. ............................ 604/94; 604/173; 604/284
[58] Field of Search ..................... 604/73, 27, 35, 604/93, 94, 173, 264, 280, 284, 902, 28, 49, 54; 128/200.26

[56] References Cited

U.S. PATENT DOCUMENTS

| | | | |
|---|---|---|---|
| 2,052,321 | 8/1936 | Smart | 604/94 |
| 2,575,513 | 11/1951 | Fox | 604/35 |
| 2,945,495 | 7/1960 | Griffin | 604/93 |
| 4,573,965 | 3/1986 | Russo | 604/35 |
| 4,748,984 | 6/1988 | Patel | 128/658 |
| 4,787,894 | 11/1988 | Turnbull | 604/73 |
| 4,813,931 | 3/1989 | Hauze | 604/73 |
| 5,037,403 | 8/1991 | Garcia | 604/280 |
| 5,279,599 | 1/1994 | Wilk | 604/280 |
| 5,322,521 | 6/1994 | Wilk | 604/53 |
| 5,334,167 | 8/1994 | Cocanower | 604/280 |
| 5,353,787 | 10/1994 | Price | 128/200.26 |
| 5,425,724 | 6/1995 | Akins | 604/284 |

OTHER PUBLICATIONS

Fordham, Stewart D., "Controlling Intraoperative and Post-operative Nasal Bleeding", Plastic and Reconstructive Surgery, vol. 90 No. 5 pp. 915–917 (Nov. 1992).
Haberman II, Rex S., "The Haberman suction elevator", Otolaryngology–Head and Neck Surgery, vol. 101 (6) pp. 707–708 (1989).
Haraldsson, P.-O., "Removable Suction Elevator", Plastic & Reconstructive Surgery, vol. 87, No. 4 pp. 807 (1991).
Freeman, Jeremy L., "Operative Techniques in Otolaryngology–Head and Neck Surgery" Merocel Corp., vol. 4, No. 2 (1993).

Primary Examiner—Corrine M. McDermott
Assistant Examiner—N. Kent Gring
Attorney, Agent, or Firm—Brumbaugh, Graves, Donohue & Raymond

[57] ABSTRACT

The present invention relates to a method and apparatus for suctioning the sinonasal tract of a subject, wherein at least one suction tube is passed through the oral cavity into the nasal tract, to extend at least as far as the nasopharynx.

29 Claims, 10 Drawing Sheets

5,599,304

SINONASAL SUCTION APPARATUS

SPECIFICATION

This invention relates to a method and apparatus for suctioning the sinonasal tract via the oral cavity, wherein the apparatus is inserted through the oral cavity into the nasal tract, at least as far as the nasopharynx, and optionally into the nasal choanae or nasal cavities during surgery on the sinonasal tract. In this way, a posterior approach is used to provide suction to the sinonasal tract.

BACKGROUND OF THE INVENTION

The development and widespread use of many different devices used to suction the nasal cavities have served to focus on the shortcomings and problems to be solved in the design of suction devices used for this purpose. Although there have been many improvements in their design, several problems have not been overcome.

All the devices until the present invention use an 'anterior' route, i.e. an approach via the nostrils, or nares, to suction the nasal tract. This approach is fraught with problems, which occur in patients having either normal or pathological anatomical structure of the anterior nasal tract. In patients having a narrow nasal cavity or a severely deviated septum, anterior suction devices described in the prior art cannot be used prior to or early during the surgical procedure for correction of the defect. Thus, at the stage of the surgical procedure when most needed, suction is not available to facilitate the surgery. Even in a patient with large nostrils, a suction tube inserted into a nasal cavity through a nostril substantially obstructs the entrance to the operating field, as sinonasal surgery is usually performed through the nostrils. It is vital to remove blood and debris that accumulate in the nasal tract during surgery in order to maintain a clear surgical field. Therefore, the surgery is frequently interrupted to permit suctioning through the nostrils.

A further disadvantage of the traditional method of suctioning the nasal cavities through the nostrils is that blood drains posteriorly into the throat. To prevent blood reaching the throat, traditionally gauze packing is placed in the throat via the oral cavity of an anesthetized patient prior to surgery. Once the gauze packing is saturated with blood, blood leaks into the throat, from where it passes into the patient's gastro-intestinal tract, resulting in postoperative nausea and vomiting as well as inaccurate measurements of surgical blood loss.

The advantages of the suction apparatus of the invention are manifold. It allows the possibility of continuous suctioning of the nasal tract, thus preventing the unwanted accumulation of blood, secretions or debris in the operating field. Because the suction apparatus of the invention passes through the oral cavity, and not the nostrils, it leaves the nostrils (i.e. the access to the operating field) completely clear and does not obstruct the surgical field, thus greatly eliminating interruptions during surgery to suction the sinonasal tract. Further, the suction apparatus of the invention eliminates the necessity of having a gauze throat pack with all its attendant disadvantages. By allowing for continuous suctioning (or intermittent, if preferred) of the nasopharynx, blood, secretions and debris are suctioned into the suction tubing and do not accumulate in the throat. Thus, blood does not pass into the stomach and accurate measurement of intraoperative—and postoperative, if necessary—blood loss is possible.

An unexpected advantage of the invention is a reduction of swelling of the skin around the nose during surgery. This is achieved when the suction apparatus is in place, as the skin on the nose is "sucked down" onto the nasal skeleton, thus reducing swelling. The greater the swelling, the greater is the distortion of the nose during surgery. This is particularly important during cosmetic nasal surgery, as the surgeon must predict, intraoperatively, the postoperative appearance.

Also advantageously, once the suction apparatus of the invention is properly placed, it requires little or no manipulation, leaving the hands of the surgeon and assistants free to perform other functions.

A further advantage of the invention relates to the fact that the oral cavity, the nasopharynx and the nasal choanae are capable of receiving a wider-bore tube than are the nostrils. In this regard, the larger the diameter of the tube, the more effective is the suctioning mechanism. Thus, the present invention solves the long-felt problems and fulfills all the attendant needs existing in the field of the invention as discussed above.

SUMMARY OF THE INVENTION

The present invention is directed to a method and apparatus for suctioning the nasopharynx, nasal choanae and the remainder of the sinonasal tract. The apparatus comprises at least one hollow tube i.e. a tube having a lumen extending along the entire length of the tube for suctioning the nasal tract. The tube has an insertion end for insertion via the oral cavity at least into the high oropharynx or the nasopharynx and optionally into the nasal choanae or nasal cavities and a suction end for attachment to a suction means, the tube withstanding acute bends without kinking and about 1–5 centimeters of the tube adjacent to and including the insertion end being directed upward at an angle in relation to the remainder of the tube, said tube having at least one opening at the insertion end and at least one opening at the suction end.

The method for suctioning contents, such as blood, secretions, debris, irrigating fluid and also smoke (that accumulates following laser treatment of the nasal cavities) from the sinonasal tract comprises the steps of: (a) inserting at least one tube into the nasal tract via the oral cavity, the tube having an insertion end for insertion into the nasal tract via the oral cavity so that the insertion end extends at least as far as the nasopharynx, and a suction end for attachment to a suction means, the tube withstanding acute bends without kinking and about 1–5 centimeters of the tube adjacent to and including the insertion end being directed upward at an angle in the range of 15° to 90° in relation to the remainder of the tube, the tube having at least one opening at the insertion end and at least one opening at the suction end, (b) attaching the at least one suction tube to a suction means, (c) suctioning the nasal cavity, (d) withdrawing the tube when the nasopharynx or nasal cavities no longer require suctioning, and (e) repeating steps (a), (b) and (c) if further suctioning of the nasal cavity becomes necessary, or steps (b) and (c) if the tube has not been removed from the nasopharynx or nasal cavities.

DETAILED DESCRIPTION OF THE INVENTION

Figure 1:
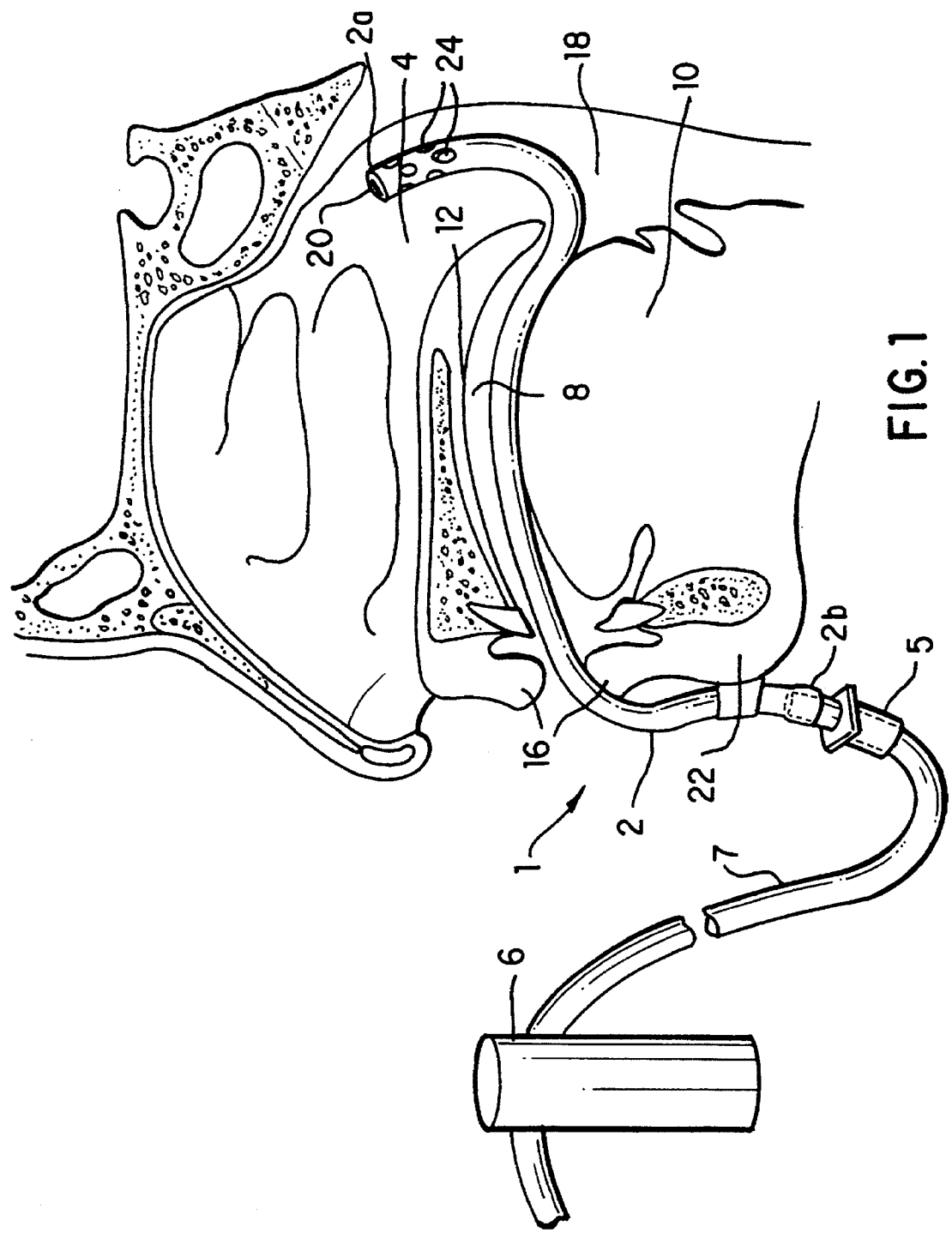
FIG. 1 is an elevational view of the suction apparatus, wherein a single suction tube is inserted into the nasopharynx, in accordance with the invention.

The present invention is directed to an apparatus for suctioning the sinonasal tract, comprising at least one hollow suction tube or catheter having an insertion end and a suction end, the tube having at least one opening near or at each end. The insertion end is for insertion into the nasal tract at least as far as the nasopharynx via the oral cavity, and the suction end is for attachment to a means for suctioning the sinonasal tract. Continuous or intermittent suction may be applied and may be adjusted and/or controlled by a foot-pedal or its equivalent, by a hand-operated device known to those skilled in the art or by any other means used in the field. In this specification, the direction of the tubes of the apparatus and the relationship of the tubes to the anatomy of a patient is described with reference to the patient in an upright position. However, it should be understood that the apparatus is usually placed and used in a patient who is in a supine or semi-sitting position. The apparatus may be placed under vision using a laryngoscope, a fiberoptic light source or any other commonly used visual aid, or it may be introduced "blind", using linear markings on the tube as a guide in achieving the desired positioning thereof. Alternatively, the length of the portion of the tube disposed within the oral cavity can be estimated to be the length required for a particular patient. After placement of the tube(s), the position of the tube(s) can be confirmed by digital palpation and then, if necessary, introduced further or partly withdrawn to achieve the required positions thereof. Furthermore, in this specification, the term "insertion end" refers to the end of the tube that is introduced from outside the patient through the lips onto the oral cavity and placed in the nasopharynx, nasal choanae or nasal cavities, and the term "suction end" refers to the end of the tube that is attached directly to a suction means, or if necessary, attached indirectly to the suction means via as much additional tubing as is necessary to reach the suction means. The term "nasopharynx" refers to the region behind the tip of the soft palate. The term "nasal tract," refers to the nasal cavities and/or the nasal choanae and/or the nasopharynx, and/or any other portion of the nasal passages well-known to one skilled in the art. The "sino-nasal tract" refers to the nasal tract which is continuous with all the paranasal sinuses, which include the maxillary, frontal, ethmoid and sphenoid sinuses and any anatomic variants thereof.

The suction tubes may have linear markings as discussed above, which indicate the length of the portion of the suction tube that has been introduced into the patient when the tube is being inserted or when the tube is in place. The portion of the tube that remains outside the oral cavity can be secured to the patient's chin for stability.

The tube or tubes of the invention have lengths and inner diameters used for children of varying ages and different-sized adults. The range of the length of tubes for pediatric use is between about 7 centimeters and about 10 centimeters, with an internal diameter in a range between about 3 millimeters and about 5.5 millimeters. For adult use, the tubes range in length from about 8 centimeters to about 20 centimeters, with an internal diameter in a range between about 4 millimeters and about 9 millimeters. In a preferred embodiment used for an average adult patient, the tube is about 16 centimeters long, has an inner lumen diameter of about 5.5 millimeters and an outer diameter of about 6.5 millimeters. Optionally, the tube may be longer, as the length of the tube is not critical to the invention. The contours of the portion of the tube that is disposed within the oral cavity and the nasal tract substantially conform to the anatomy of the tongue, palate and nasal tract. For approximately 11–15 centimeters extending from the suction end of the 16 centimeter tube, the tube is substantially horizontal, gently curving downwards as it passes posteriorly over the upper surface of the tongue. The remaining approximately 1–5 centimeters of the tube, extending to the insertion end of the tube, angles upward into the nasopharynx.

The suction tubes may be of uniform diameter throughout their length. Alternatively, the suction tubes may vary in diameter along their lengths. For example, the tube may be tapered so that the diameter of the insertion end is less than the diameter of the remainder of the tube. Alternatively, the insertion end may terminate in a beveled end, having an oblique outlet orifice. Finally, the insertion end of the tube may be expanded so that the diameter of the insertion end is greater than the diameter of the remainder of the tube, thus presenting a greater area for suctioning. This expanded end is especially useful for a single suction tube having its insertion end disposed in the nasopharynx. Moreover, the expanded end may be fashioned to resemble a salt-shaker, the insertion end having a cover which may be integral to the walls of the tube, the cover having several openings through which the lumen of the tube communicates with the exterior of the tube. This decreases the likelihood of suctioning the nasal mucosa into the tube or otherwise traumatizing the nasal tissues even if excessively strong suction is applied. The walls of the 1–5 centimeters at the insertion end of the tube may have one or multiple holes or suction ports connecting the lumen of the tube with the exterior of the tube. Alternatively, these multiple holes or suction ports may be disposed in the walls along the entire length of the tube, or any portion thereof. The lumen of the tube communicates with the oral cavity or the nasal tract through these holes. The relationship of the thickness of the wall of the tube to the diameter of the lumen of the tube is such that the walls of the tube will not collapse and occlude the lumen, when the nasal tract is suctioned using a suction pressure which is sufficient to remove contents of the nasal tract, as described above.

A hollow satellite tube or catheter may be piggybacked onto or otherwise attached or affixed to the outer surface of the suction tube or tubes of the invention. The satellite tube has an insertion end for insertion into the oropharynx or upper respiratory tract and a connector end for attachment to a source of, for example, oxygen or humidified air. Oxygen or any other substance can thus be administered into the oropharynx or into the respiratory tract via the satellite tube or catheter, which may be selected from suitable catheters or tubes which are used for the administration of oxygen or other substances into the respiratory tract.

In another embodiment, instead of having a suction tube with preformed curves, the suction tube is linear or almost linear. The tube has a trigger means upon the upper outer surface of the tube, the trigger means being positioned so that when the insertion end of the tube passes into the oropharynx, activation of the trigger mechanism causes an about 1–5 centimeters portion of the tube adjacent to and including the insertion end to bend and turn in an upward direction so that the insertion end is positioned in the nasopharynx or choanae as required. This portion of the tube at the insertion end forms an angle of about 15° to 90° in relation to the remainder of the tube. Anatomically, right and left nasal choanae serve as conduits from the respective side of the nasal cavity into the common nasopharynx posteriorly. In order to be positioned in the choanae, the angled portion of the tubes must be longer than the angled portion of a tube to be positioned in the nasopharynx of the same patient.

The most preferred embodiment of the invention is a suction apparatus having two tubes, wherein the portion of the tubes projecting upward into the nasopharynx are of a sufficient length to advance through the nasopharynx into the nasal choanae so that the insertion end of the left tube is disposed in the left choana and the insertion end of the right tube is disposed in the right choana. Optionally the insertion ends may be disposed in the back of the nasal cavities. The tubes may join to form one tube at any point between the point at which the tubes angle upwards and the suction end of the tubes. Alternatively, the two tubes may remain separate until they enter the arms of a "Y" shaped connector that leads directly, or indirectly via additional tubing, into a suction means. The two tubes may remain separate up to and including their respective attachments to the suction means. Where the two tubes enter the suction means via a Y-connector or additional tubing, the apparatus may comprise a means whereby each tube can be individually closed off, so that either the left or right nasal choana can be suctioned independently of and separately from the other.

In another embodiment of the invention, each suction tube has a sump tube which enters the suction tube from the outside and is disposed within the lumen of the suction tube. The sump tube has a first end which is open to atmospheric air and a second end which opens into the lumen of the suction tube at or near the insertion end of the suction tube. The second end of the sump tube is closer to the insertion end of the suction tube and the point of entry of the sump tube into the lumen of the suction tube is closer to the suction end of the suction tube. Firstly, the sump tube prevents the suction tube from suctioning nasal tissue and secondly, it prevents mstrong or excessive suction from causing collapse of the walls of the suction tube with obliteration of its lumen and failure of the suction mechanism.

Any movement of the suction tubes such as twisting, rotating or shifting from the desired position in the oral cavity may cause the tubes to shift within the nasopharynx or nasal cavities or even be displaced therefrom. Such potential malposition of the tube(s) is prevented by stabilization of the tube(s). For example, in a preferred embodiment of the invention, attachments project from both sides of the tube onto the upper surface of the tongue, stabilizing the tube in relation to the tongue when the tube has been placed in the desired position. Similarly, attachments to stabilize the tubes in relation to the tongue may be used in an embodiment of the invention having two suction tubes. The attachment from the left suction tube projects laterally onto the left side of the upper surface of the tongue and the attachment from the right suction tube projects laterally onto the right side of the upper surface of the tongue. In yet another embodiment, the suction tube or tubes are secured by a clamp, or any other suitable attachment means, to an endotracheal tube which has been inserted into a patient, thus using the endotracheal tube to stabilize the suction tubes. Finally, the suction tube or tubes may be disposed on the floor of the mouth between the tongue and medial aspect of the mandible or alternatively in the gingivo-buccal sulcus. Moreover, two suction tubes, one on either side of the tongue, may be attached to each other by a bridging attachment which is disposed on the upper surface of the tongue.

In any of the previously described embodiments of the invention, the suction tubes may have a sponge or other absorbable material attached on the outer surface of the tubes in the vicinity of the oropharynx, nasopharynx and/or nasal choanae. The sponge or other absorbent material traps and/or absorbs blood, secretions, debris etc. that fail to enter the opening at the insertion end or the side-holes of the tubes. The sponge may be disposed on only a part of the outer surface of the tubes or it may encircle the tubes and may occlude the oropharyngeal and/or nasopharyngeal cavity at various levels. Certain sponges, for example MEROCEL®, which expand or swell only when exposed to moisture, are preferable for use with the tubes of the invention because it is easy to insert suction tubes having a collapsed dry sponge into the pharynx. As the sponge expands only on contacting saliva and other secretions in the mouth and pharynx the tube can be manipulated into position before the sponge is fully expanded. The position of the tube can then be ascertained by the user, and adjusted if necessary. After insertion of the tube, expansion of the sponge can be expedited by spraying it with saline or any other fluid prior to ascertaining its position. Alternatively, a balloon, instead of a sponge, may be used to occlude the oropharyngeal and/or nasopharyngeal cavity at the desired level. When a suction tube having an attached balloon is introduced into the oral cavity, the balloon is in a deflated state. After the suction tube has been placed in the desired position, the balloon is inflated to occlude the oropharyngeal and/or nasopharyngeal cavity, thus preventing blood, secretions, bone and other debris from passing down into the oesophagus or upper respiratory tract.

The tubes of the invention may be made from natural rubber, synthetic rubber, plastics and thermoplastics including, but not limited to, polyvinylchloride, polyethylene or the like, or malleable metals that can be premolded into various shapes including, but not limited to, aluminum or stainless steel. The tube may be made from any inert materials used in this field, and the materials used may be opaque or clear. The tube may have preformed contours or it may be made from a material having sufficient flexibility to allow the tube or portions thereof to conform, as necessary, to the anatomical contours of the oral cavity, tongue, palate, oropharynx, and nasal tract. The material used must allow a portion of the tube to be bent so that it forms an acute angle in relation to the remainder of the tube without the tube kinking, and the material may have sufficient resilience to allow the tube to resume the preformed shape following manipulations of the tubes.

This invention is also directed to a method for suctioning the sinonasal tract, comprising the steps of (a) inserting at least one tube via the oral cavity into the nasal tract at least as far as the nasopharynx, the tube having an insertion end and a suction end, the insertion end for insertion into the nasal tract via the oral cavity so that the insertion end is inserted at least as far as the nasopharynx and the suction end for attachment to a suction means, said tube withstanding acute bends without kinking and about 1–5 centimeters of the tube adjacent to and including the insertion end being directed upward at an angle in relation to the remainder of the tube, said tube having at least one opening at or near the insertion end and at least one opening at the suction end, (b) attaching the suction end of the at least one suction tube to a suction means, and (c) suctioning the nasal cavity.

In accordance with the invention, there is also a method provided for suctioning the sinonasal tract, comprising (a) providing a suction tube having an insertion end for insertion into the nasal tract via the oral cavity so that the insertion end extends at least as far as the nasopharynx, and a suction end for attachment to a suction means, said tube withstanding acute bends without kinking and about 1–5 centimeters of the tube adjacent to and including the insertion end being directed upward at an angle in relation to the remainder of the tube, said tube having at least one opening near the insertion end and at least one opening at the suction end, (b) providing a nasal catheter which has (1) a first end for inserting into a nose of a patient via a nares and a second end for remaining outside the body and (2) an external diameter that is smaller than the internal diameter of the suction tube for the patient, (c) inserting the first end of the via a nares into the nose of the patient nasal catheter until the first end passes into the oral cavity at least as far as the oropharynx (d) introducing a forceps or a finger of a user into the oropharynx of the patient and withdrawing the first end into the mouth and through the lips to the exterior (e) threading the insertion end of the suction tube over the first end of the nasal catheter so that the insertion end of the suction tube is disposed in the nasal tract at least as far as the nasopharynx, (f) pulling on the second end of the nasal catheter until the first end is withdrawn out of the nose through the nares (g) attaching the suction end of the suction tube to a suction means, and (h) suctioning the nasal tract.

The present invention will further be described with reference to FIGS. 1 to 17.

FIG. 1 shows a suction apparatus 1 of the invention in the desired position in a patient. The suction apparatus 1 comprises a hollow suction tube 2 having an insertion end 2a situated in the nasopharynx 4 and a suction end 2b connected to a suctioning means 6 via a connector 5 and additional tubing 7. The contours of the portion of the suction tube 2 lying within the oral cavity 8 substantially conform to the anatomy of the tongue 10, the palate 12 and the nasopharynx 4. The portion of the tube 2 extending from the lips 16 over the tongue 10 is substantially horizontal, gently curving downwards as it passes posteriorly into the throat 18. The remaining about 1–5 centimeters of the tube that terminate at the insertion end are directed upwards forming an angle relative to the remainder of the tube in the range of about 15° to 90°, preferably from about 30° to 60°, so that the opening 20 of the insertion end of the tube is disposed in the nasopharynx 4. The tube may be secured to the chin 22 so that it remains firmly in place. The multiple side holes 24 allow for additional suction ports, thus increasing the effectiveness of the suctioning mechanism. Further, if one hole becomes blocked with debris, suctioning can still be performed through the other holes.

Figure 2:
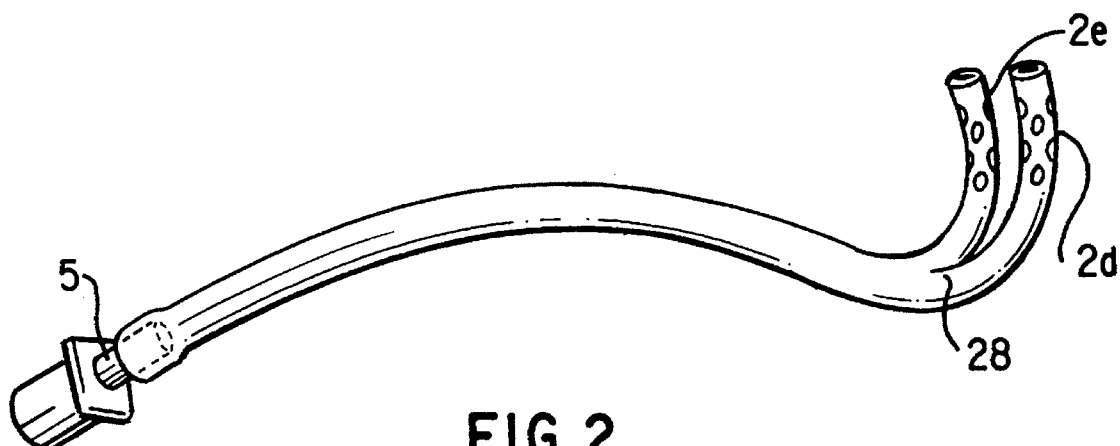
FIG. 2 is an elevational view of suction tubes, where two tubes at the insertion end unite to form one tube at the point of angulation of the tubes, in accordance with the invention.

FIG. 2 shows an embodiment of the invention wherein there are two suction tubes 2d and 2e, the insertion end of the tube 2d for insertion into the left nasal choana and the insertion end of the tube 2e for insertion into the right nasal choana. The two tubes 2d and 2e join to form a single hollow tube at point 28 which is in the vicinity of the point of angulation of the tubes towards the nasopharynx. The suction end of the tube is shown to connect to a connector 5.

Figure 3:
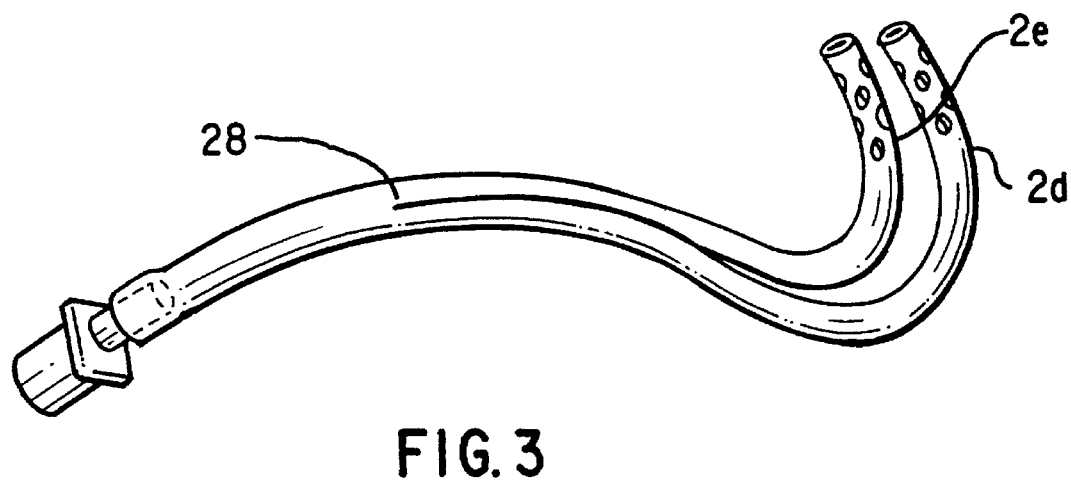
FIG. 3 is an elevational view of the suction tubes as shown in FIG. 2, wherein the point at which the two tubes unite to form one tube is closer to the suction end of the tube, in accordance with the invention.

FIG. 3 shows an embodiment of the invention wherein the tubes 2d and 2e join to form a single hollow tube at point 28, which is closer to the suction end than in FIG. 2.

Figure 4:
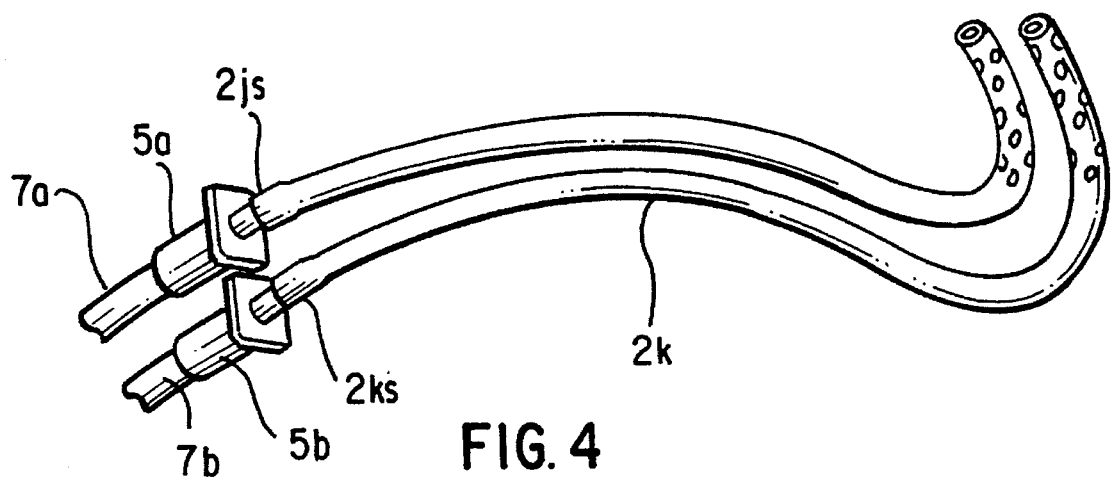
FIG. 4 is an elevational view of suction tubes, wherein the two tubes remain separate throughout their course, in accordance with the invention.

FIG. 4 shows an embodiment of the invention wherein suction tubes 2j and 2k remain separate up to an including their suction ends 2j$_s$ and 2k$_s$, each attaching to separate connectors 5a and 5b, the connectors attaching to additional tubing 7a and 7b that attach to the suction means (not shown).

Figure 5:
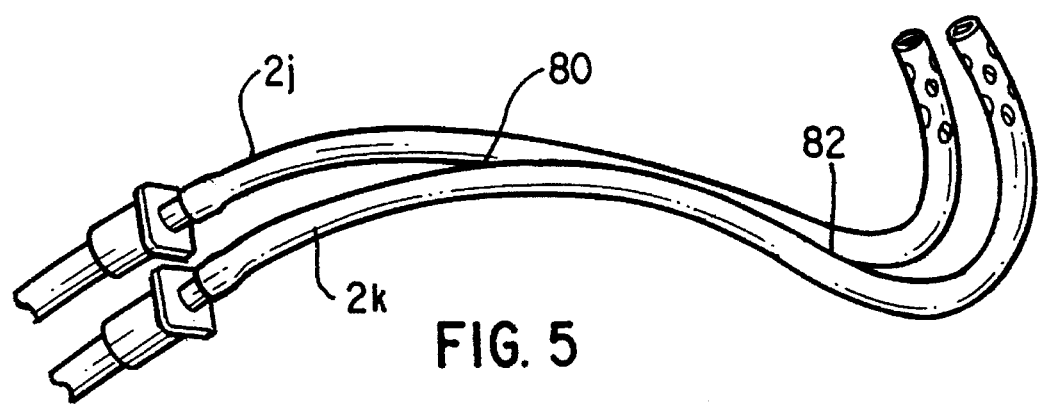
FIG. 5 is an elevational view of the suction tubes shown in FIG. 4, wherein a part of the intraoral portion of each tube are anchored together, in accordance with the invention.

FIG. 5 shows the 2 suction tubes 2j and 2k shown in FIG. 4, wherein part of the intraoral portions of tubes 2j and 2k are anchored together from point 80 to point 82 to promote stability of the tubes and decrease the potential for rotation and movement of the tubes 2j and 2k.

Figure 6:
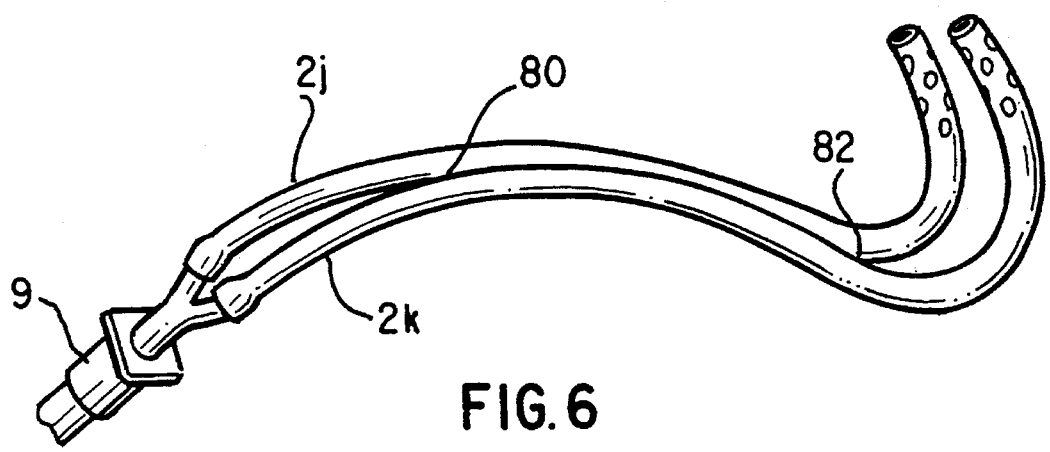
FIG. 6 is an elevational view of the suction tubes shown in FIG. 5, wherein the suction ends of the tubes attach to a single connector, in accordance with the invention.

FIG. 6 shows the suction tubes 2j and 2k as illustrated in FIG. 5, wherein both tubes 2j and 2k attach to a single "Y" shaped connector 9. The use of the single connector 9 allows even less movement of the tubes 2k and 2j in relation to each other, thus further increasing the stability of the suction apparatus.

Figure 7:
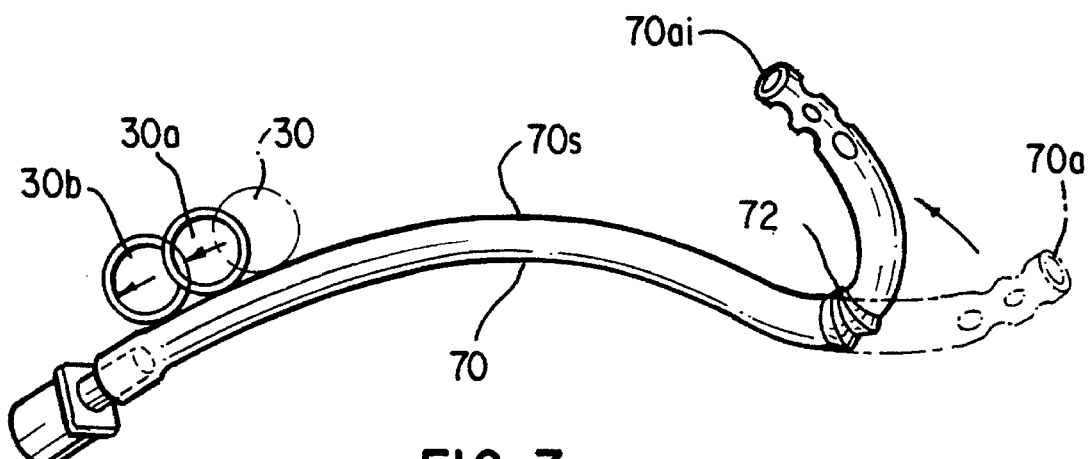
FIG. 7 is an elevational view of an almost linear suction tube, which has a trigger means on its upper surface, in accordance with the invention.

FIG. 7 shows an embodiment of the invention wherein an almost linear tube 70 is introduced into the oral cavity. A trigger means 30 is disposed on the upper outer surface 70s of the tube 70. When the trigger means 30 is activated to position 30a, the portion of the tube adjacent to the insertion end bends and turns in an upward direction, the angle 72 decreases, and the tube 70 adopts position 70a$_i$; when the trigger means is further activated to position 30b, the angle 72 decreases further.

Figure 8:
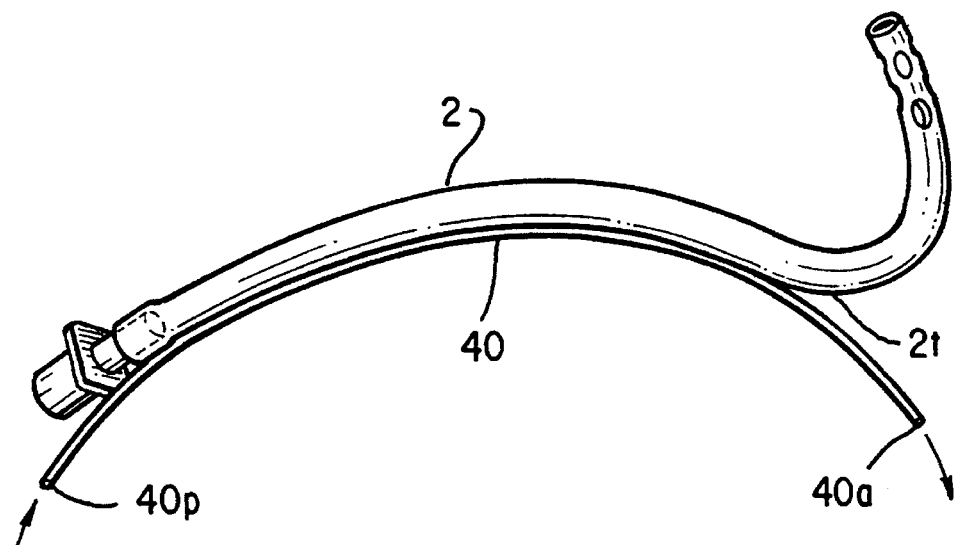
FIG. 8 is an elevational view of a suction tube, having a satellite tube for carrying oxygen, in accordance with the invention.

FIG. 8 shows a satellite hollow tube 40 affixed onto the lower outer surface 2t of the tube 2, tube 40 having an insertion end 40a for insertion into the oropharynx or upper respiratory tract, and a connector end 40p for attachment to an oxygen source.

Figure 9:
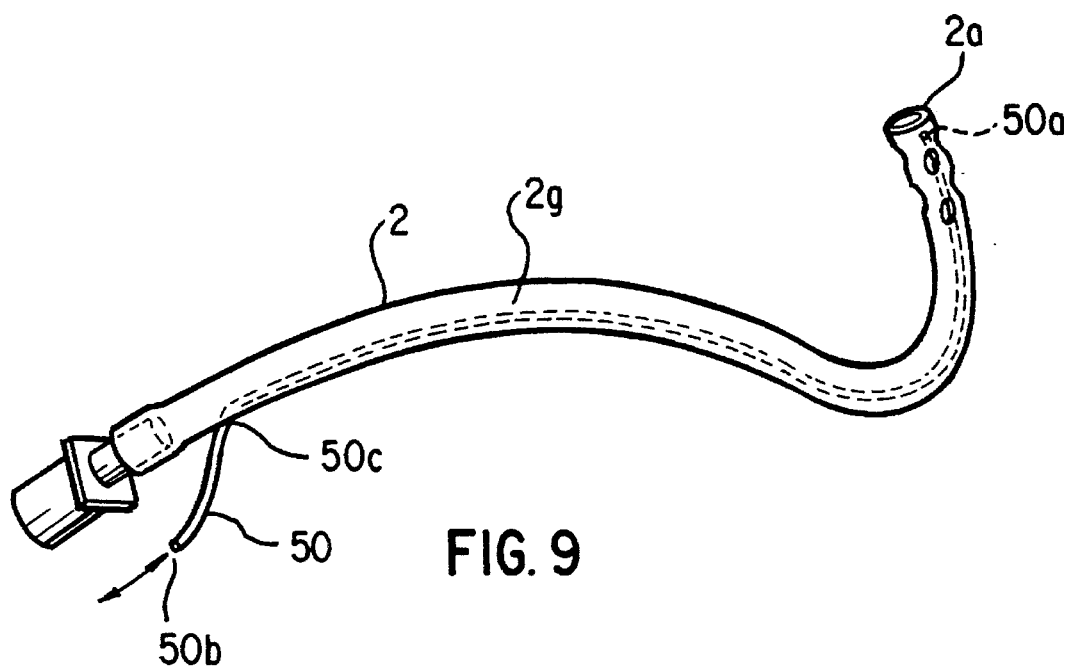
FIG. 9 is an elevational view of a suction tube, having a sump tube, in accordance with the invention.

FIG. 9 shows an embodiment of the invention wherein a suction tube 2 has a second hollow tube 50 which enters the suction tube 2 at point 50c and remains within the lumen 2g of the suction tube 2 up to the point 50a where the second hollow tube 50 opens into the lumen of the suction tube 2 close to the insertion end 2a of the suction tube 2. The other end 50b of tube 50 is left open to atmospheric air. The entry of tube 50 into the lumen of tube 2 as shown at 50c can occur at any convenient point between the suction and the insertion end of suction tube 2.

Figure 10:
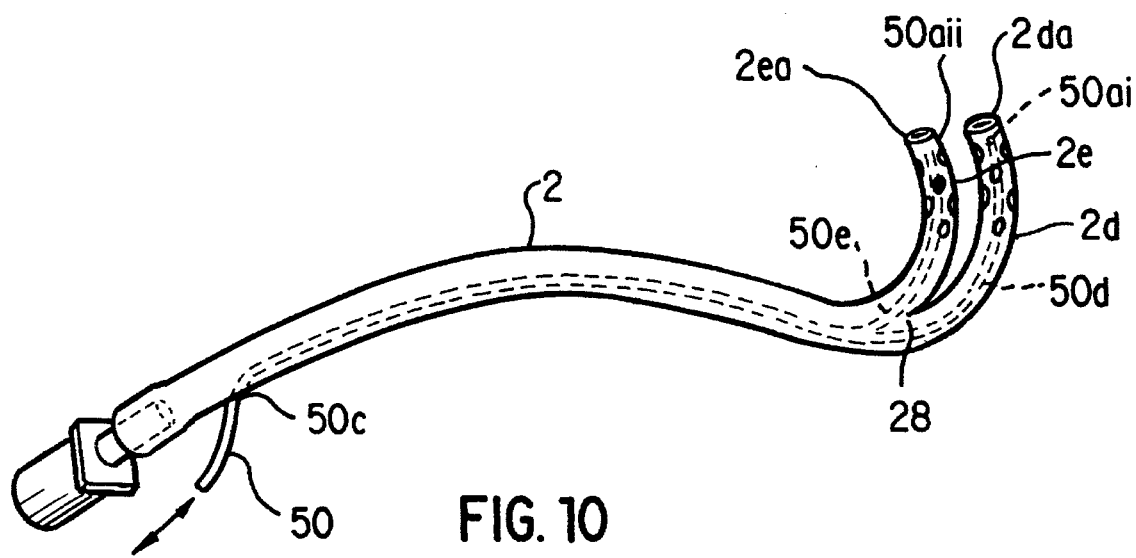
FIG. 10 is an elevational view of the suction tubes as shown in FIG. 2, having sump tubes, in accordance with the invention.

FIG. 10 shows an embodiment of the invention wherein the second hollow tube 50 shown in FIG. 9 is used in the suction apparatus shown in FIG. 2. The tube 50 enters the suction tube 2 at point 50c and while within the lumen of tube 2 and after the point of junction 28 of tubes 2d and 2e to form tube 2, the tube 50 divides into two tubes, 50d and 50e. Tube 50d enters into tube 2d and opens at point 50a$_i$ into the lumen of the tube 2d close to the insertion end 2da of tube 2d. Tube 50e enters into tube 2e and opens at point 50a$_{ii}$ into the lumen of tube 2e close to the insertion end 2e$_a$ of tube 2e.

Figure 11:
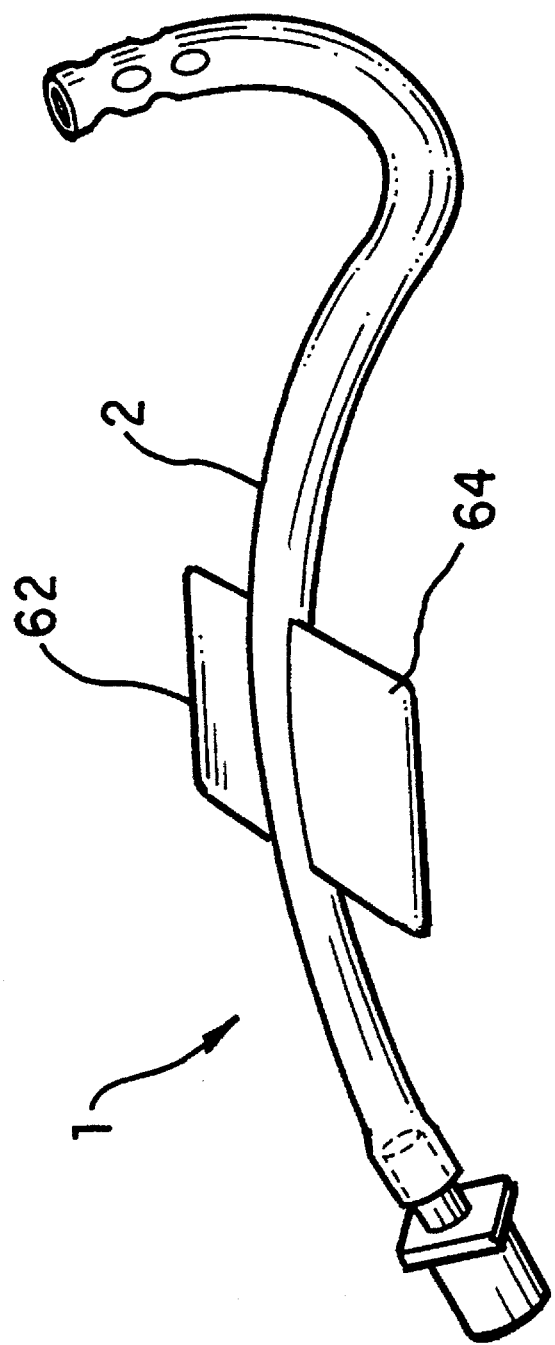
FIG. 11 is an elevational view of a suction tube having projections on both sides of the tube, in accordance with the invention.

FIG. 11 illustrates the suction apparatus shown in FIG. 1 wherein two attachments 62 and 64 of the portion of the suction tube 2 overlying the tongue project laterally, attachment 62 projecting onto the right upper surface of the tongue, and attachment 64 onto the left upper surface of the tongue, in such a way that attachments 62 and 64 stabilize the tube 2 in relation to the tongue and prevent the tube 2 from twisting, rotating or otherwise moving in the oral cavity after the tube 2 is placed in the desired position. It is to be understood that attachments 62 and 64 may be employed in any of the embodiments of this invention as herein described.

Figure 12:
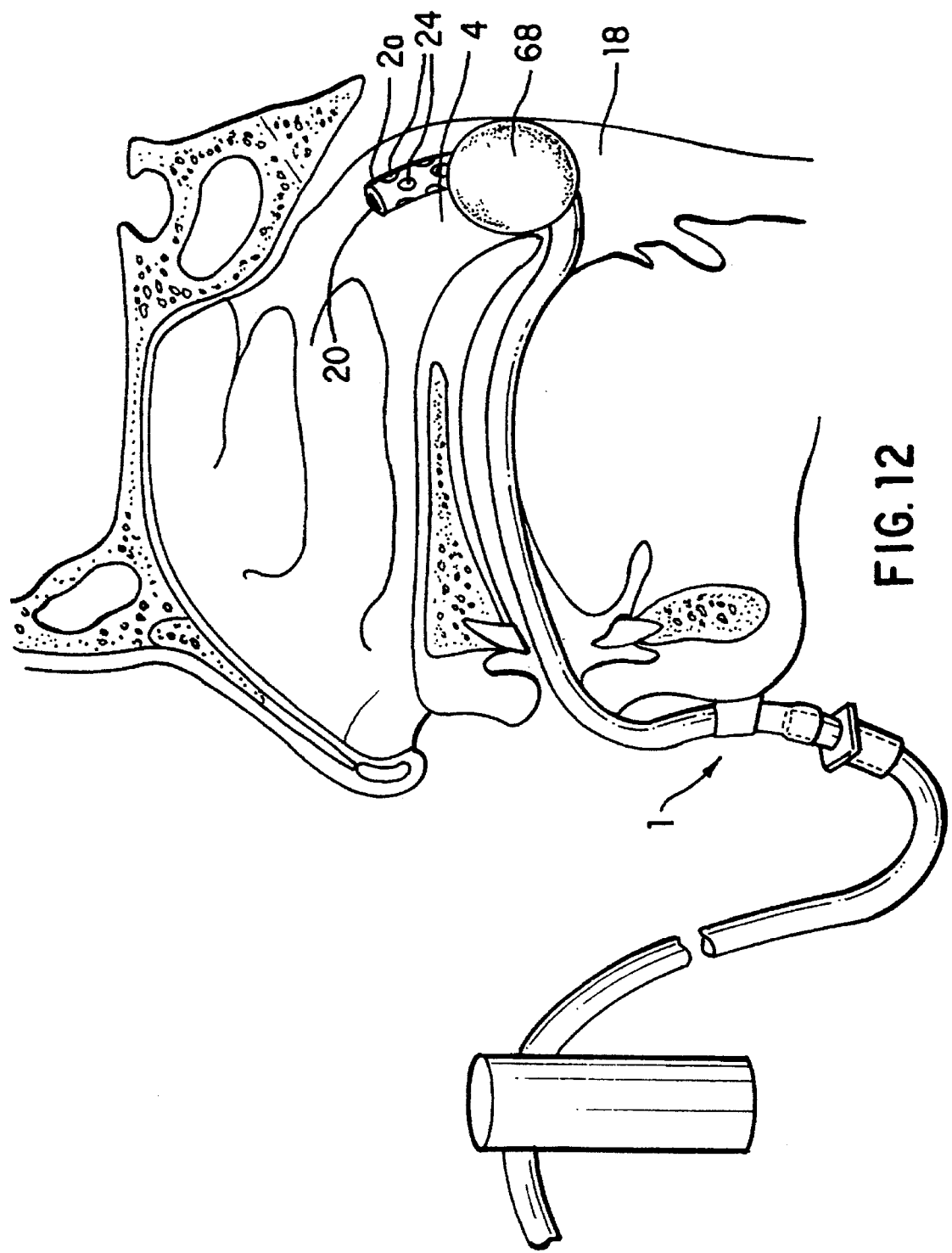
FIG. 12 is an elevational view of a suction tube having a sponge attached to its outer surface in the area of the oropharynx and nasopharynx.

FIG. 12 illustrates the suction apparatus 1 shown in FIG. 1, wherein the suction tube 2 has a sponge 68 attached to the outer surface of the portion of the tube disposed in the oropharynx 18 and the nasopharynx 4. The sponge 68 obliterates the oro-pharyngeal and naso-pharyngeal cavities, thus preventing the contents of the cavity 4 above the sponge passing into the cavity 18 below the sponge. The sponge traps and absorbs blood, secretions and debris that fail to enter the opening 2o at the insertion end 2a of the tube 2 or the side-holes 24 of the tube.

Figure 13:
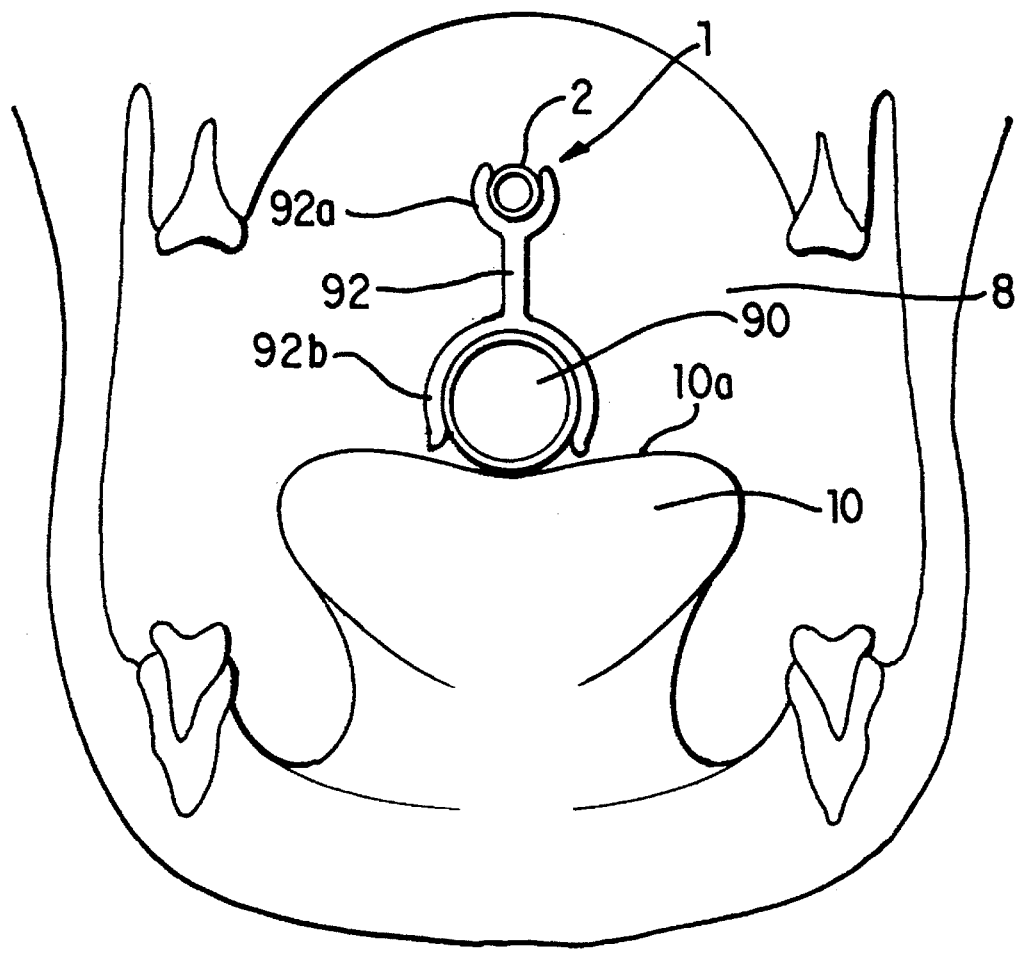
FIG. 13 is a cross-sectional view of a suction tube of the invention anchored to an endotracheal tube, in accordance with the invention.

FIG. 13 illustrates a cross-sectional view of a tube 2 of a suction apparatus 1 of the invention and an endotracheal tube 90 in the oral cavity 8 of a patient shown in sagittal section. The endotracheal tube 90 is disposed on the upper surface 10a of the tongue 10 and the suction tube 2 is secured to the endotracheal tube 90 by a double clamp 92, the upper clamp 92a holding the suction tube 2 and the lower clamp 92b holding the endotracheal tube 90. Thus, the suction tube 2 is stabilized in relation to the endotracheal tube 90 which is in a stable position in relation to the tongue 10.

Figure 14:
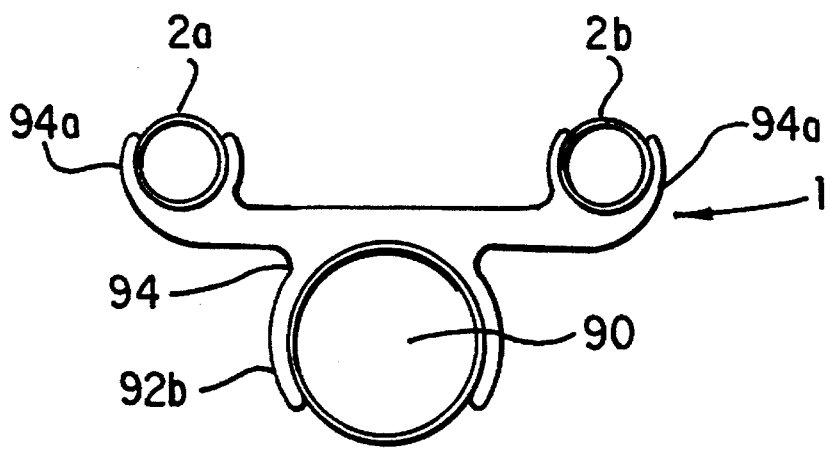
FIG. 14 is a cross-sectional view of suction tubes of the invention anchored to an endotracheal tube, in accordance with the invention.

FIG. 14 illustrates a cross-sectional view of suction tubes 2a and 2b of a suction apparatus 1 of the invention secured to an endotracheal tube 90 by a multiple-clamp device 94, the upper two clamps 94a holding the two suction tubes 2a and 2b and the lower clamp 94b holding the endotracheal tube 90.

Figure 15:
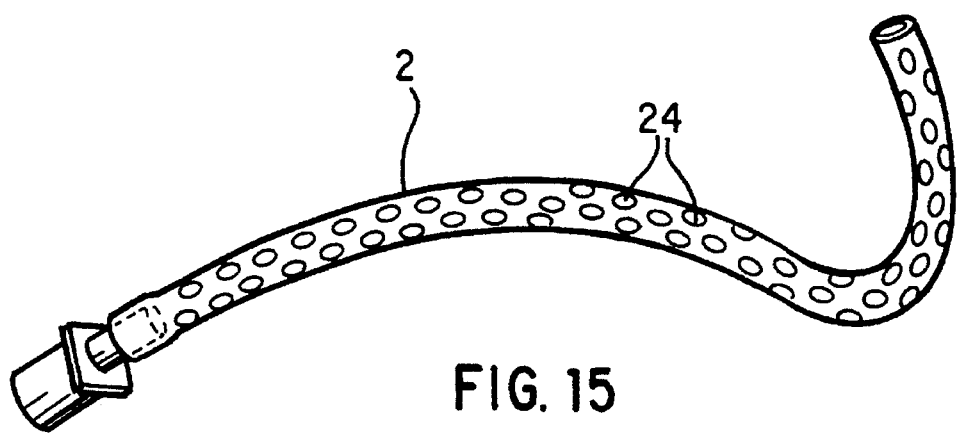
FIGS. 15–17 are elevational views of suction tubes having holes in the walls over varying portions of the tubes, in accordance with the invention.
Figure 16:
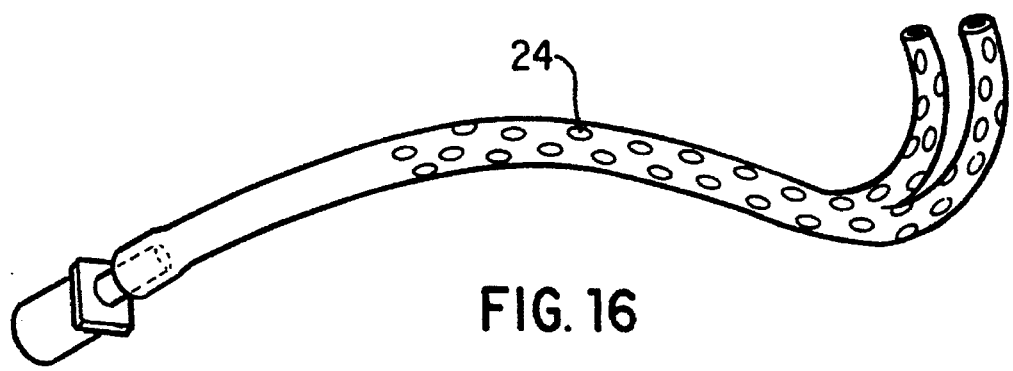
Figure 17:
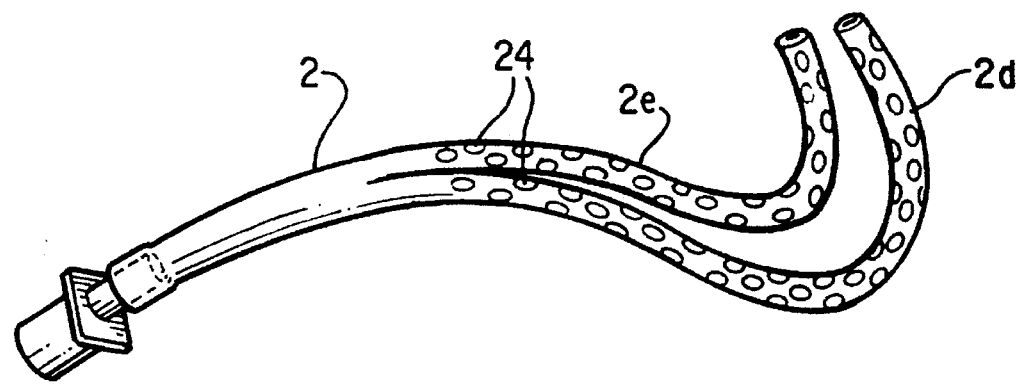

FIG. 15, 16 and 17 show embodiments of the invention wherein transluminal multiple side holes or suction ports 24 extend over different lengths of the tube 2 or tubes 2d and 2e.

Figure 18:
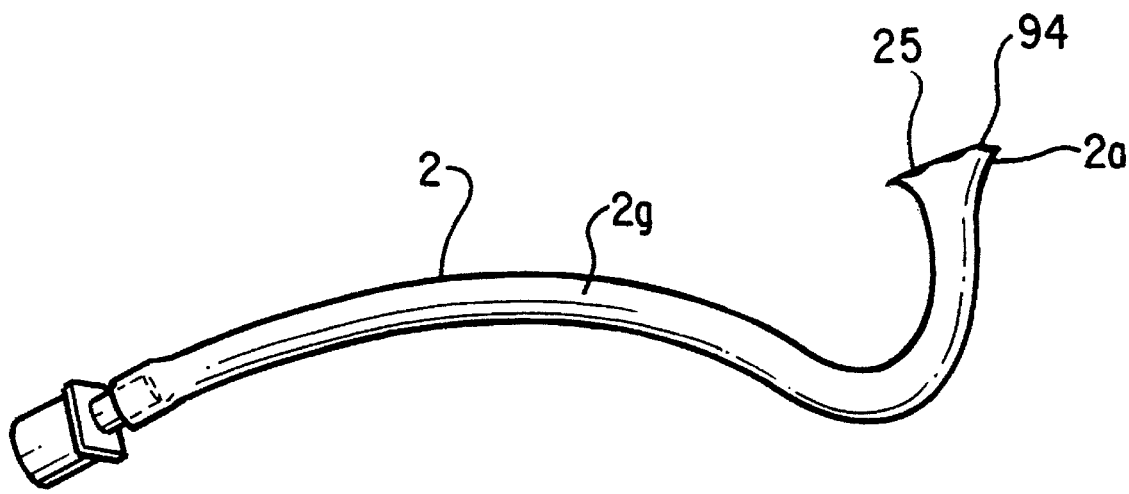
FIG. 18 is an elevational view of a suction tube having an expanded covered insertion end, in accordance with the invention.

FIG. 18 shows an embodiment of the invention wherein the insertion end 2a of the tube 2 is expanded and has a cover 94, the cover 94 being attached to the tube 2 round the circumference of the tube 2 at the insertion end 2a. The covering has multiple holes 25 that allow the lumen 2g of the tube 2 to communicate with the exterior of the tube.

Figure 19:
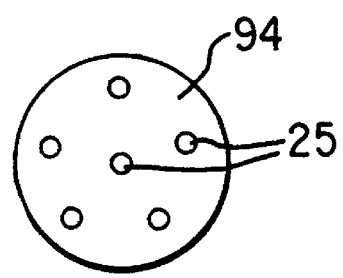
FIG. 19 is an enlarged view of the covered expanded insertion end of the tube shown in FIG. 18.

FIG. 19 shows an enlarged view of the cover 94 over the insertion end 2a of the tube 2 as shown in FIG. 18, the cover 94 having multiple holes.

The description of the above embodiments is meant to be illustrative of the scope and spirit of the invention. These embodiments will make apparent other embodiments and examples which are within contemplation of this invention.

I claim:

1. A suction apparatus for suctioning the sinonasal tract comprising:

at least one hollow suction tube having an insertion end for insertion into the nasal tract of a subject via the oral cavity so that, when placed in the subject, the insertion end extends at least as far as the nasopharynx, and a suction end for attachment to a suction means, wherein about 1–5 centimeters of the suction tube adjacent to and including the insertion end is directed upward at an angle in relation to the remainder of the suction tube, said suction tube having at least one opening at the insertion end and at least one opening at the suction end, and a lumen between the insertion end and the suction end which allows the suctioning of the sinonasal tract, wherein the suction tube is substantially linear, the suction tube having a trigger means on the upper outer surface of the tube, wherein activation of the trigger means causes the about 1–5 centimeters of the suction tube including and adjacent to the insertion end to angle upwards at least into the nasopharynx.

2. A suction apparatus for suctioning the sinonasal tract comprising:

at least one hollow suction tube having an insertion end for insertion into the nasal tract of a subject via the oral cavity so that, when placed in the subject, the insertion end extends at least as far as the nasopharynx, and a suction end for attachment to a suction means, wherein about 1–5 centimeters of the suction tube adjacent to and including the insertion end is directed upward at an angle in relation to the remainder of the suction tube, said suction tube having at least one opening at the insertion end and at least one opening at the suction end, and a lumen between the insertion end and the suction end which allows the suctioning of the sinonasal tract, wherein a sump tube passes through the wall of the suction tube and is disposed in the lumen of the suction tube, the sump tube having one end which is open to atmospheric air and a second end which opens into the lumen of the suction tube close to the insertion end of the suction tube.

3. A suction apparatus for suctioning the sinonasal tract comprising:

at least one hollow suction tube having an insertion end for insertion into the nasal tract of a subject via the oral cavity so that, when placed in the subject, the insertion end extends at least as far as the nasopharynx, and a suction end for attachment to a suction means, wherein about 1–5 centimeters of the suction tube adjacent to and including the insertion end is directed upward at an angle in relation to the remainder of the suction tube, said suction tube having at least one opening at the insertion end and at least one opening at the suction end, and a lumen between the insertion end and the suction end which allows the suctioning of the sinonasal tract, wherein the suction tube has a sponge attached to the outer surface of the suction tube, which, when placed in the subject, is positioned in the vicinity of the oropharynx and the nasopharynx.

4. A suction apparatus for suctioning the sinonasal tract comprising:

at least one hollow suction tube having an insertion end for insertion into the nasal tract of a subject via the oral cavity so that, when placed in the subject, the insertion end extends at least as far as the nasopharynx, and a suction end for attachment to a suction means, wherein about 1–5 centimeters of the suction tube adjacent to and including the insertion end is directed upward at an angle in relation to the remainder of the suction tube, said suction tube having at least one opening at the insertion end and at least one opening at the suction end, and a lumen between the insertion end and the suction end which allows the suctioning of the sinonasal tract, wherein the insertion end of the suction tube is expanded so that the diameter of the suction tube at the insertion end is greater than the diameter of the remainder of the suction tube, and wherein a cover is disposed over the insertion end, the cover being attached at its periphery to the wall of the suction tube, the cover having several openings.

5. A method for suctioning the sinonasal tract, comprising the steps of:

(a) inserting at least one tube via the oral cavity into the nasal tract at least as far as the nasopharynx, the tube having an insertion end for insertion into the nasal tract via the oral cavity so that the insertion end is inserted at least as far as the nasopharynx, and a suction end for attachment to a suction means, said tube withstanding acute bends without kinking and about 1–5 centimeters of the tube adjacent to and including the insertion end being directed upward at an angle in relation to the remainder of the tube, said tube having at least one opening near the insertion end and at least one opening at the suction end;

(b) attaching the suction end of the at least one suction tube to a suction means, and (c) suctioning the nasal cavity.

6. A method for suctioning the sinonasal tract, comprising the steps of:

(a) providing a suction tube having an insertion end for insertion into the nasal tract via the oral cavity so that the insertion end extends at least as far as the nasopharynx, and a suction end for attachment to a suction means, said tube withstanding acute bends without kinking and about 1–5 centimeters of the tube adjacent to and including the insertion end being directed upward at an angle in relation to the remainder of the tube, said tube having at least one opening near the insertion end and at least one opening at the suction end;

(b) providing a nasal catheter which has (1) a first end for inserting into a nose of a patient via a nares and a second end for remaining outside the body and (2) an external diameter that is smaller than the internal diameter of the suction tube for the patient;

(c) inserting the first end of the via a nares into the nose of the patient nasal catheter until the first end passes into the oral cavity at least as far as the oropharynx;

(d) introducing a forceps or a finger of a user into the oropharynx of the patient and withdrawing the first end into the mouth and through the lips to the exterior;

(e) threading the insertion end of the suction tube over the first end of the nasal catheter so that the insertion end of the suction tube is disposed in the nasal tract at least as far as the nasopharynx;

(f) pulling on the second end of the nasal catheter until the first end is withdrawn out of the nose through the nares;

(g) attaching the suction end of the suction tube to a suction means, and (h) suctioning the sinonasal tract.

7. A method for suctioning the sinonasal tract according to claim 5 or 6, wherein the tube has at least one additional opening in its wall, this additional opening allowing further communication between the lumen of the tube and the exterior of the tube.

8. A method for suctioning the sinonasal tract according to claim 5 or 6, wherein the apparatus comprises a first and a second tube, the insertion end of the first tube being inserted into a left nasal choana and the insertion end of the second tube being inserted into a right nasal choana, the suction ends of the first and second tubes being connected to the suction means.

9. A method for suctioning the sinonasal tract according to claim 8, wherein a part of the intra-oral portions of the tubes are attached to each other by anchoring means.

10. A method for suctioning the sinonasal tract according to claim 5 or 6, wherein multiple openings extend along substantially the entire length of the tube.

11. A method for suctioning the sinonasal tract according to claim 8, wherein each tube comprises a further step for individually closing off the suction mechanism for that tube, thereby allowing the right and left nasal choanae to be suctioned separately.

12. A method for suctioning the sinonasal tract according to claim 5 or 6, wherein the diameter of the tube is the same throughout its length.

13. A method for suctioning the sinonasal tract according to claim 5 or 6, wherein the tube is tapered so that the diameter of the insertion end of the tube is less than the diameter of the remainder of the tube.

14. A method for suctioning the sinonasal tract according to claim 5 or 6, wherein the insertion end of the tube is expanded, so that the diameter of the insertion end is greater than the diameter of the remainder of the tube.

15. A method for suctioning the sinonasal tract according to claim 5 or 6, wherein each tube bears linear markings, each linear marking indicating the length of the tube from the insertion end of the tube.

16. A method for suctioning the sinonasal tract according to claim 5 or 6, wherein the contours of the suction tube are preformed to substantially conform to the contours of the tongue, palate and nasopharynx.

17. A method for suctioning the sinonasal tract according to claim 5 or 6, wherein the suction tube is substantially linear, the suction tube having a trigger means on the upper outer surface of the tube, wherein activation of the trigger means causes the about 1–5 centimeters of the tube including and adjacent to the insertion end to angle upwards at least into the nasopharynx.

18. A method for suctioning the sinonasal tract according to claim 5 or 6, wherein the length of the suction tube is in a range between about 12 centimeters and about 18 centimeters, the diameter of the suction tube is in a range between about 4.5 millimeters and about 8.5 millimeters, and about 1–5 centimeters of the tube adjacent to and including the insertion end is angled upward in relation to the remainder of the tube.

19. A method for suctioning the sinonasal tract according to claim 18, wherein the length of the suction tube is about 16 centimeters and the diameter of the suction tube is about 5.5 millimeters.

20. A method for suctioning the sinonasal tract according to claim 5 or 6, wherein a hollow satellite tube is affixed onto the outer surface of the suction tube, the satellite tube having an insertion end having at least one opening and a connector end having at least one opening, the insertion end for insertion into the oropharynx or upper respiratory tract and the connector end for attachment to an oxygen source.

21. A method for suctioning the sinonasal tract according to claim 5 or 6, wherein a sump tube passes through the wall of the suction tube and is disposed in the lumen of the suction tube, the sump tube having one end which is open to atmospheric air and a second end which opens into the lumen of the suction tube close to the insertion end of the suction tube.

22. A method for suctioning the sinonasal tract according to claim 21, wherein the two tubes join close to the suction ends to form one tube, the one tube attaching to a suction means.

23. A method for suctioning the sinonasal tract according to claim 22, wherein the angle is between about 30° and 60°.

24. A method for suctioning the sinonasal tract according to claim 5 or 6, wherein the tube has a sponge attached to the outer surface of the tube in the vicinity of the oropharynx and the nasopharynx.

25. A method for suctioning the sinonasal tract according to claim 5 or 6, wherein the angle of the about 1–5 centimeters of the tube adjacent to and including the insertion end is at an angle in the range of between about 15° and 90° in relation to the remainder of the tube.

26. A method for suctioning the sinonasal tract according to claim 5 or 6, wherein the insertion end is expanded so that the diameter at the insertion end is greater than the diameter of the remainder of the tube, and wherein a cover is disposed over the insertion end, the cover being attached at its periphery to the wall of the tube, the cover having several openings.

27. A suction apparatus for suctioning the sinonasal tract comprising:

at least two hollow suction tubes, each having an insertion end for insertion into the nasal tract of a subject via the oral cavity so that, when placed in the subject, the insertion end extends at least as far as the nasopharynx and a suction end for attachment to a suction means;

wherein the insertion end of the first suction tube being inserted into a left nasal choana and the insertion end of the second suction tube being inserted into a right nasal choana;

wherein about 1–5 centimeters of each suction tube adjacent to and including the insertion end is directed upward at an angle in relation to the remainder of the suction tube;

each suction tube having at least one opening at the insertion end and at least one opening at the suction end and a lumen between the insertion end and the suction end which allows the suctioning of the sinonasal tract;

the suction ends of the first and second suction tubes being connected to the suction means;

and wherein each suction tube is substantially linear and has a trigger means on the upper outer surface of the suction tube, wherein activation of the trigger means causes the about 1–5 centimeters of the suction tube including and adjacent to the insertion end to angle upwards at least into the nasopharynx.

28. A suction apparatus for suctioning the sinonasal tract comprising:

at least two hollow suction tubes, each having an insertion end for insertion into the nasal tract of a subject via the oral cavity so that, when placed in the subject, the insertion end extends at least as far as the nasopharynx and a suction end for attachment to a suction means;

wherein the insertion end of the first suction tube being inserted into a left nasal choana and the insertion end of the second suction tube being inserted into a right nasal choana;

wherein about 1–5 centimeters of each suction tube adjacent to and including the insertion end is directed upward at an angle in relation to the remainder of the suction tube;

each suction tube having at least one opening at the insertion end and at least one opening at the suction end and a lumen between the insertion end and the suction end which allows the suctioning of the sinonasal tract;

the suction ends of the first and second suction tubes being connected to the suction means; and wherein a sump tube passes through the wall of each suction tube and is disposed in the lumen of the suction tube, the sump tube having one end which is open to atmospheric air and a second end which opens into the lumen of the suction tube close to the insertion end of the suction tube.

29. A suction apparatus for suctioning the sinonasal tract comprising:

at least two hollow suction tubes, each having an insertion end for insertion into the nasal tract of a subject via the oral cavity so that the insertion end extends at least as far as the nasopharynx and a suction end for attachment to a suction means;

wherein the insertion end of the first suction tube being inserted into a left nasal choana and the insertion end of the second suction tube being inserted into a right nasal choana;

wherein about 1–5 centimeters of each suction tube adjacent to and including the insertion end is directed upward at an angle in relation to the remainder of the suction tube;

each suction tube having at least one opening at the insertion end and at least one opening at the suction end and a lumen between the insertion end and the suction end which allows the suctioning of the sinonasal tract;

the suction ends of the first and second suction tubes being connected to the suction means; and wherein each suction tube has a sponge attached to the outer surface of the suction tube in the vicinity of the oropharynx and the nasopharynx.

* * * * *

UNITED STATES PATENT AND TRADEMARK OFFICE
CERTIFICATE OF CORRECTION

PATENT NO. : 5,599,304
DATED : February 4, 1997
INVENTOR(S) : Christopher M. Shaari It is certified that error appears in the above-indentified patent and that said Letters Patent is hereby corrected as shown below:

Col. 6, line 18, "mstrong" should read --strong--;

Col. 7, line 59, "via a nares into the nose of the patient nasal catheter" shoud read --nasal catheter via a nares into the nose of the patient--;

Col. 8, line 40 "an including" should read --and including--;

Col. 10, line 3 "round" should read --around--;

Col. 11, lines 62-63, "via a nares into the nose of the patient nasal catheter" should read --nasal catheter via a nares into the nose of the patient--.

Signed and Sealed this

Third Day of June, 1997

Attest:

BRUCE LEHMAN

*Attesting Officer*    *Commissioner of Patents and Trademarks*